United States Patent [19]

Puskas et al.

[11] Patent Number: 4,537,985

[45] Date of Patent: Aug. 27, 1985

[54] PROCESS FOR THE MANUFACTURE OF 1,4-BIS[2-(4'-CARBOMETHOXYSTYRENYL)] BENZENE

[75] Inventors: Imre Puskas, Wheaton; Marshall Schmitt, Chicago, both of Ill.

[73] Assignee: Standard Oil Company (Indiana), Chicago, Ill.

[21] Appl. No.: 514,681

[22] Filed: Jul. 18, 1983

Related U.S. Application Data

[63] Continuation-in-part of Ser. No. 369,035, Apr. 16, 1982, abandoned.

[51] Int. Cl.$^3$ .................. C07C 67/00; C07F 9/54
[52] U.S. Cl. .................................. 560/96; 560/76; 568/9
[58] Field of Search .................. 560/76, 96; 568/9

[56] References Cited

U.S. PATENT DOCUMENTS

| | | | |
|---|---|---|---|
| 2,612,516 | 9/1952 | Heimsch et al. | 560/96 |
| 3,076,020 | 1/1963 | Stilz et al. | 560/89 |
| 3,177,208 | 4/1965 | Stilz et al. | 560/76 X |
| 4,179,578 | 12/1979 | Fleck et al. | 560/76 |

FOREIGN PATENT DOCUMENTS

| | | |
|---|---|---|
| 1108219 | 6/1961 | Fed. Rep. of Germany . |
| 1129947 | 5/1962 | Fed. Rep. of Germany . |
| 1134064 | 8/1962 | Fed. Rep. of Germany . |
| 913735 | 12/1962 | United Kingdom . |
| 924762 | 5/1963 | United Kingdom . |

*Primary Examiner*—Natalie Trousof
*Assistant Examiner*—Vera C. Clarke
*Attorney, Agent, or Firm*—Gunar J. Blumberg; William T. McClain; William H. Magidson

[57] ABSTRACT

A process for the manufacture of 1,4-bis[2-(4'-carbomethoxystyrenyl)] benzene is disclosed. This process comprises reacting, at a temperature of about 0° C. to about 100° C., in a highly polar anhydrous organic solvent or solvent mixture, or in liquid ammonia, a p-xylylene-bis-(trialkylphosphonium halide) or p-xylylene-bis-(triarylphosphonium halide) with 4-carbomethoxybenzaldehyde, initiated by the slow introduction of an organometallic compound or an inorganic base. Polyesters, such as polyethylene terephthalate, are copolymerized with about 5 to about 20 parts per million of 1,4-bis[2-(4'-carbomethoxystyrenyl)] benzene. 1,4-bis[2-(4'-carbomethoxystyrenyl)] benzene is useful to provide permanent whiteness to polyesters and polyamides and other synthetic or natural polymers. Polyesters are useful for the manufacture of fibers, films, and related industrial products.

11 Claims, No Drawings

PROCESS FOR THE MANUFACTURE OF 1,4-BIS[2-(4'-CARBOMETHOXYSTYRENYL)] BENZENE

This is a continuation-in-part application of Ser. No. 369,035, filed Apr. 16, 1982.

FIELD OF THE INVENTION

This invention relates to the manufacture of 1,4-bis-[2-(4'-carbomethoxystyrenyl)]benzene, hereinafter referred to as CMSB. Its chemical structure is shown below:

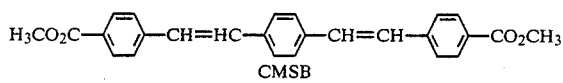

CMSB

CMSB and its derivatives are useful optical brighteners. CMSB was found to be particularly effective for the brightening of polyester fibers by chemical incorporation (copolymerization) of trace amounts of CMSB into the polyesters.

This invention relates to the manufacture of CMSB by treating xylylene dichloride with triphenylphosphine to form p-xylylene bis-(triphenylphosphonium chloride), which, when reacted with 4-carbomethoxybenzaldehyde in the presence of an alkali metal alkoxide, forms the CMSB in very high yields. CMSB, manufactured according to our process, is a mixture of cis-cis, cis-trans and trans-trans geometrical isomers of CMSB.

BACKGROUND

CMSB was first synthesized in 1959 by Campbell and McDonald, reported in *J. Org. Chem.* 24,1246 (1959). The following references relate to certain uses and syntheses of CMSB: German Pat. No. 1,108,219; German Pat. No. 1,129,947; German Pat. No. 1,134,064; British Pat. No. 913,735; British Pat. No. 924,762; U.S. Pat. No. 3,076,020; U.S. Pat. No. 3,177,208. None of the references disclosed suggests our novel process for the manufacture of CMSB.

Although the cited references indicate that CMSB can be prepared by various routes, for commercial production a process is desirable which is simple, gives a high yield of product and uses commercially available starting materials. The following process meets these criteria: The reaction of alpha,alpha'-dihalo-p-xylene with two moles of triphenyl phosphine gives p-xylylene-bis-(triphenyl-phosphonium halide) in nearly quantitative yield. This compound is converted to a Wittig reagent with a strong base, for example sodium methoxide or another alkoxide, in the presence of 4-carbomethoxybenzaldehyde. The Wittig reagent immediately reacts with two moles of 4-carbomethoxybenzaldehyde to give CMSB. The process scheme becomes practicable due to the fact that 4-carbomethoxybenzaldehyde, or by other name methyl 4-formyl benzoate (MFB), is a by-product of dimethyl terephthalate synthesis and is available on a commercial scale. Although the purity of this commercial by-product is low and the impurities are difficult to remove, we have found that the purity can be increased to a level wherein the impurities become innocuous. The impurities are dimethyl terephthalate and methyl benzoate, and neither of them interferes in the desired reaction of MFB.

The first step of the synthetic scheme, the reaction of alpha,alpha'-dichloro-p-xylene with triphenyl phosphine has been described in the literature using dimethyl formamide solvent. We have found that the reaction can be carried out without a solvent, in the melt, at 100°–200° C., for 0.5 to 5 hours.

According to our novel process for the manufacture of 1,4-bis-[2-(4'-carbomethoxystyrenyl)]-benzene, we react, at a temperature of about 0° C. to about 100° C., in a highly polar, anhydrous organic solvent or solvent mixture, or in liquid ammonia, a p-xylene-bis-(trialkylphosphonium halide) or p-xylylene-bis-(triarylphosphonium halide) with 4-carbomethoxybenzaldehyde initiated by the slow introduction of an organo metallic compound or an inorganic base. The molar ratio of p-xylylene-bis-(trialkylphosphonium halide) or p-xylylene-bis-(triarylphosphonium halide), the 4-carbomethoxybenzaldehyde and the organo metallic compound, or an inorganic base, ranges from about 1.0:2.0:2.0 to about 1.0:2.2:2.8. Useful p-xylylene, bis-trialkyl or triaryl phosphonium halides include: trimethyl phosphonium halides, triethyl phosphonium halides, tripropyl phosphonium halides, tributyl phosphonium halides, triphenyl phosphonium halides, tribiphenyl phosphonium halides and etc. Useful organic phosphonium halides are the chlorides, bromides, and iodides. Solvents useful in our process are toluene, ethanol, methanol, diethyl ether, tetrahydrofuran, dimethylformamide, dimethylsulfoxide, xylene, benzene, and mixtures of these or liquid ammonia and etc. Useful organo metallic compounds include: phenyl lithium, butyl lithium, sodamide, potassium amide, sodium methoxide, sodium ethoxide, potassium ethoxide, sodium carbonate, and potassium carbonate. Useful inorganic bases include sodium hydroxide, ammonium hydroxide and etc.

In a preferred embodiment of our novel process for the manufacture of CMSB, p-xylylene-bis-(triphenyl-phosphonium chloride) and methyl-4-formyl benzoate (MFB) are dissolved in a suitable solvent, such as pure, dry dimethylsulfoxide, dimethylformamide, or mixture of an aromatic solvent (benzene, toluene, xylenes, etc.) with aliphatic alcohols (absolute methanol, absolute ethanol, etc.). The resulting mixture is stirred extensively and slowly, a solution of an alkali metal alkoxide, such as methanolic sodium methoxide, is introduced dropwise. Conveniently, the reaction temperature can be ambient, or between 0° C. and the reflux temperature of the solvent. The reagents are used in almost stoichiometric quantities. The reaction is almost quantitative. Isolated yields of CMSB (by crystallization) are above 80%; higher isolated yields can be obtained with the use of pure reagents (e.g., using pure MFB and not a commercial source of MFB).

The CMSB obtained in this synthesis is a mixture of cis-cis, cis-trans and trans-trans isomers. The individual geometrical isomers need not be separated. However, for identification purposes, we have separated all the isomers by recrystallization procedures and identified them by their melting points. IR spectra, $^1$H NMR spectra, $^{13}$C NMR spectra and mass spectra.

The isomeric mixture of CMSB, as well as the individual isomers, can be hydrolized to the diacid. This, in turn, can easily be converted to the diacid dichloride with thionyl chloride. This latter compound can serve as a monomer or co-monomer for the synthesis of fluorescent polyamides.

CMSB is particularly useful as an optical brightener for polyesters, polyamides and other polymers, including natural products, such as cotton. The optical brightening effect is shown in the tables. The individual geometrical isomers of CMSB, and an isomeric mixture of CMSB, were copolymerized into polyethyleneterephthalate (hereinafter PET) at 20 parts per million level. Higher levels are not useful since the polyester polymer loses the optical qualities, however, at least three parts per million of CMSB are needed. The characterizations, the color measurements and the UV degradation studies of these polymers are summarized in Tables I and II, respectively.

As Table I indicates, the physical and chemical properties of the polymers (inherent viscosity, carboxyl content, diethylene glycol content) were essentially identical, without and with incorporation of CMSB, and were not dependent on the geometrical isomer of the CMSB used.

However, the fluorescence spectra of the polyethyleneterephthalates made with CMSB were quite different than those of the blank PET containing no CMSB. The excitation maxima and emission maxima of the brightened polyesters were at the same wavelength and not dependent on the geometrical isomer of CMSB used. The location of the excitation maxima, 407 nm, measured by reflectance on the solid polymer, differed from that of the CMSB isomers (375 nm) measured in $CH_2Cl_2$ solutions. The differences may arise either from the phase of the fluorescing materials or, alternatively, from the chemical changes. The fluorescence intensities of the brightened polyesters differed with the CMSB isomer used in the synthesis. In the case of CMSB monomers, the trans-trans isomer had the highest fluorescence intensity and the cis-cis isomer had the lowest.

Table II summarizes the results of the instrumental color measurements. The L value of the tristimulus color measures the greyness (100=white; 0=black); the a value the red-green hue (red is +; green is —); and the b value the yellow-blue hue (yellow is +; blue is —). The measurements taken on the Diano instrument—which filters out the UV light and hence eliminates the fluorescence—give practically identical color values for the blank and the brightened polymers. The results indicate that the individual geometrical isomers of CMSB gave almost the same color improvement. The color improvements are noticeable even to the naked eye. The b values of Table II show that the incorporation of 20 ppm CMSB into polyethylene terephthalate overcompensates for the yellowness, and the polymer becomes bluish. Probably 3 to 15 ppm CMSB would suffice to compensate for the yellowness and would provide the whitest appearance to the polymer. It is interesting that, while CMSB itself is a yellow compound, its incorporation at trace levels into polyethylene terephthalate removes the yellowness from the polymer by fluorescence.

In the polyesters of Table I, the 20 ppm CMSB has been chemically incorporated into the polymer. Incorporating more than 20 ppm CMSB is detrimental, as is incorporating less than 3 ppm. To support our conclusions concerning the copolymerization of CMSB, the following experiments were carried out: The polymers of Table I were extracted with refluxing toluene in a Soxhlet apparatus to see whether the CMSB can be "extracted out" of the polyethyleneterephthalate. If it were selectively extractable, this would indicate that the CMSB was not chemically incorporated into the polymer. On the other hand, if it were not extractable, the results still would not conclusively prove that it is incorporated because the trans-trans isomer of CMSB is known to be extremely insoluble in solvents which do not attack polyethyleneterephthalate.

Toluene did not attack the polyethyleneterephthalate. The extraction did not result in a weight loss of polyethyleneterephthalate. On the contrary, a 4 to 5 percent weight increase was measured after vacuum drying at 70° C. Apparently, the polyesters adsorbed some toluene. The extracted polyesters became opaque, while originally they were transparent. Table III compares the tristimulus color values of the original with those of the extracted polyesters. The results clearly indicate that the brightener was not removed from the samples.

Table III illustrates that CMSB is incorporated into PET as a copolymer. On the basis of our evaluations, we believe that it is critical to incorporate 3 to 20 ppm of CMSB into commercial PET to compensate for the yellowness of the polymer. Outside this range, CMSB loses its ability to remove the yellow color from the polymers. This level of incorporation is much lower than currently used in polyester fibers. Thus, CMSB is a very outstanding brightener for polyesters. The outstanding brightening effect may be associated with the fact that the excitation maxima of the brightened polyesters is probably at an optimal wavelength (407 nm, see Table I), just at the end of the visible range. Natural light has this wavelength in fairly high intensity, thus providing strong excitation for the fluorescence. Also, the emission maximum of the brightened polyesters is at the right wavelength (443 nm, see Table I), which means emission of blue light. The fluorescence intensities are high.

CMSB is also useful to brighten polyamide and polyimide polymers and other synthetic and natural polymers, such as polymethylmethacrylate, cotton, linen, viscose, etc.

The following examples illustrate the preferred embodiment of this invention. It will be understood that these examples are for illustration purposes only and do not purport to be wholly definitive with respect to the conditions or scope of this invention.

EXAMPLES

Example I p-Xylylene-bis-(triphenylphosphonium chloride)

Alpha, alpha'-dichloro-p-xylene (10.01 g) and triphenylphosphine (31.19 g) were dissolved in dimethylformamide by heating. The solution was refluxed for two hours. White crystalline solids separated from the solution. After cooling, these were filtered and washed with a little cold dimethylformamide and then a little diethyl ether. Finally, the product was dried in a vacuum oven at 130° C. Yields were 94–95%. The salt did not melt up to 400° C.

Example II p-Xylylene-bis-(triphenylphosphonium chloride) by the "melt-process"

Alpha, alpha'-dichloro-p-xylene (7.0 grams) and triphenylphosphine (20.98 grams) were heated in an oil bath to give a melt. The liquid was stirred until it started to solidify. Heating continued even after solidification started. The mixture was kept at 160°–190° C. for one hour. After cooling, the solid product was broken up and powdered. It did not melt up to 400° C.

Example III

Purification of methyl 4-formyl benzoate (MFB)

The purity of the MFB available commercially, as a by-product of dimethyl terephthalate synthesis, is usually only 50-80%. Major impurities are dimethylterephthalate and methyl benzoate. There are also numerous minor impurities which must be removed. The crude product (200 g) was purified by recrystallization from hexane-toluene mixture (9:1, v/v, 550 ml). The white crystals were filtered, washed with hexane and dried in a vacuum oven at room temperature. (Note: heating in air leads to oxidation of the product!) The purity of the dried product was determined by gas chromatography.

Example IV

1,4-Bis-[2-(4'-carbomethoxystyrenyl)]benzene (CMSB)

To 200.09 g (0.2858 moles) of p-xylylene bis-(triphenylphosphonium chloride) were added 600 ml of absolute methanol. To this mixture was added a solution of 130.0 grams of 87 percent pure 4-carbomethoxybenzaldehyde (0.69 moles) in 600 ml toluene. The resulting mixture was stirred intensively, and 140 ml of a 25 percent methanolic sodium methoxide solution were added dropwise. The solution first became clear, but at a later stage, yellowish precipitates appeared. Following the addition of sodium methoxide, the mixture was refluxed briefly. Then heating was removed and the mixture was left standing overnight. The crystalline pale yellow product, which separated from the solution, was filtered, washed with 200 ml methanol and dried in vacuo. The yield was 110.4 g (97 percent of the theoretical yield). This product had a double melting point: part of it melted around 130° C., the rest of it around 270°-290° C. Mass spectrum indicated the molecular weight of CMSB. Thus, the product must be a mixture of isomers represented by CMSB.

From the mother liquors, at 5° C., 2.8 g additional product was isolated. This melted at 131°-134° C. and was nearly pure cis-cis isomer of CMSB. Thus, the total yield of CMSB was 99 percent. From these crops of CMSB some organic and inorganic impurities were removed by washing with hot methanol and hot water, respectively.

Example V

Separation of the geometrical isomers of CMSB

The isomeric mixture was extracted in a Soxhlet apparatus with toluene. After 29 hours of extraction, the residue left in the extraction thimble was essentially pure trans-trans isomer. This isomer melted with decomposition around 310° C. The pure trans-trans isomer has low solubility even in the most powerful organic solvents, such as dimethylformamide, etc.

The toluene extract had all the isomers, but the cis-cis isomer appeared to be the major one. The separation by fractional crystallization was extremely difficult. Using carbon tetrachloride, or carbon tetrachloride-methanol mixture, occasionally fairly pure isomers were obtained. The most difficult separation by fractional crystallization was to isolate the cis-trans isomer. The cis-cis isomer melted at 132°-134° C.; the cis-trans isomer at 160°-162° C.

Example VI

Hydrolysis of CMSB
1,4-bis-[2-(4'-carboxystyrenyl)]-benzene

Potassium hydroxide (10.0 grams) was dissolved in distilled water (20 ml), and ethanol (140 ml) was added, followed by 14.5 grams of powdered CMSB (an isomeric mixture). The mixture was refluxed for 18 hours. Then the solvents were removed from the solid-solution mixture. The residue was dissolved in 500 ml distilled water. Some trace amounts of insolubles were removed by filtration. The filtrate was acidified with concentrated hydrochloric acid solution. The precipitates were filtered, washed with large amounts of hot water, and dried in vacuum at 150° C. The yellow product did not melt up to 400° C., but around 300° C. it appeared to give partial melting with resolidification. Calculated acid number for $C_{24}H_{18}O_4$ (MW370.38): 303 mg KOH per gram. Found: 312 mg KOH per gram.

Example VII

1,4-Bis-[2-(4'-chloroformylstyrenyl)]-benzene

To 3.0 grams of 1,4-bis-[(2-(4'-carboxystyrenyl)]-benzene was added 35 ml of thionyl chloride and one drop of pyridine. The mixture was refluxed for 30 minutes. Then the thionyl chloride was removed by vacuum distillation. The residue partially crystallized. This was treated with 3 ml hexane-benzene (1:1; v/v). The insoluble yellow crystals were filtered, washed with a little hexane-benzene and dried in vacuo. This fraction, 1.0 gram, melted at 142°-149° C. It was characterized, as the expected diacid dichloride, by its IR spectrum and mass spectrum. From the mother liquors of this crop, after addition of hexane at 7° C., syrupy crops were obtained. The solvents were decanted from the syrups. Vacuum drying gave a solid foam (1.4 grams). The IR spectra and mass spectra confirmed the expected diacid dichloride assignment. The various crops probably differ in their isomeric composition.

TABLE I

Physical Properties of the Polyethylene Terephthalates Made Without and With Copolymerization of 20 ppm of the Geometrical Isomers of CMSB[a]

| ID No. | CMSB Isomer | Inh. Viscosity (dl/g) | Carboxyl End Group (mequ./kg) | Diethylene Glycol Content % |
|---|---|---|---|---|
| 5860-106 | nil (blank) | 0.45 | 13.1 | 3.4 |
| 5860-108 | cis-cis | 0.44 | 15.9 | 3.4 |
| 5860-110 | cis-trans | 0.51 | 13.6 | 3.5 |
| 5860-102 | trans-trans | 0.51 | 19.1 | 3.4 |
| 5860-104 | mixture | 0.47 | 13.7 | 3.3 |

| ID No. | CMSB Isomer | Fluorescence Spectrum[b] | | |
|---|---|---|---|---|
| | | $Ex_{max}$ | $Em_{max}$ | FI |
| 5860-106 | nil (blank) | 340 | 389 | 0.73 |
| 5860-108 | cis-cis | 407 | 444 | 2.65 |
| 5860-110 | cis-trans | 407 | 443 | 3.75 |
| 5860-102 | trans-trans | 408 | 443 | 1.80 |
| 5860-104 | mixture | 407 | 442 | 2.51 |

[a]The polymers were prepared from terephthalic acid and ethylene glycol at 275° C. under identical conditions
[b]Measured on solid PET by reflectance.

TABLE II

Tristimulus Color Values of Polyethylene Terephthalates Made Without and With Copolymerization of 20 ppm of the Geometrical Isomers of CMSB

| Identification No. | Isomer of CMSB | L | a | b |
|---|---|---|---|---|
| | | Tristimulus Color On Diano Instrument | | |
| 5860-106 | nil (blank run) | 87.3 | −1.2 | 4.7 |
| 5860-108 | cis-cis | 83.5 | −1.7 | 4.2 |
| 5860-110 | cis-trans | 88.1 | −1.5 | 4.3 |
| 5860-102 | trans-trans | 87.2 | −1.4 | 4.4 |
| 5860-104 | mixture | 86.7 | −1.4 | 4.3 |
| | | Tristimulus Color On Gardner Instrument | | |
| 5860-106 | nil (blank run) | 83.5 | −2.0 | +4.0 |
| 5860-108 | cis-cis | 79.1 | −1.0 | −1.5 |
| 5860-110 | cis-trans | 84.6 | −0.4 | −2.0 |
| 5860-102 | trans-trans | 83.4 | −0.4 | −1.7 |
| 5860-104 | mixture | 83.0 | −0.4 | −2.1 |

TABLE III

Tristimulus Color Values of Polyethylene Terephthalates Optically Brightened with CMSB Before and After Toluene Extraction[a]

| Identification No. | Isomer of CMSB | L | a | b |
|---|---|---|---|---|
| | | Tristimulus Color (Gardner Instrument) Before Extraction | | |
| 5860-106 | nil (blank run) | 83.5 | −2.0 | +4.0 |
| 5860-108 | cis-cis | 79.1 | −1.0 | −1.5 |
| 5860-110 | cis-trans | 84.6 | −0.4 | −2.0 |
| 5860-102 | trans-trans | 83.4 | −0.4 | −1.7 |
| 5860-104 | mixture | 83.0 | −0.4 | −2.1 |
| | | Tristimulus Color (Gardner Instrument) After Extraction | | |
| 5860-106 | nil (blank run) | 84.2 | −2.3 | +2.9 |
| 5860-108 | cis-cis | 79.8 | −1.6 | −1.9 |
| 5860-110 | cis-trans | 86.0 | −0.7 | −2.8 |
| 5860-102 | trans-trans | 84.6 | −0.9 | −2.3 |
| 5860-104 | mixture | 83.6 | −0.9 | −2.4 |

[a]The polyesters-except for the blank-contained 20 ppm CMSB.

We claim:

1. A process for the manufacture of 1,4-bis-[2-(4′-carbomethoxystyrenyl)]benzene which comprises reacting, at a temperature of about 0° C. to about 100° C., in a highly polar anhydrous organic solvent or solvent mixture, or in liquid ammonia a p-xylylene-bis—(trialkylphosphonium halide) or a p-xylylene-bis—(triarylphosphonium halide) with 4-carbomethoxybenzaldehyde, initiated by the slow introduction of an organometallic base or an inorganic base.

2. The process of claim 1 wherein the molar ratio of p-xylene-bis—(trialkylphosphonium halide) or p-xylene-bis—(triarylphosphonium halide), the 4-carbomethoxybenzaldehyde and the organometallic base or an inorganic base ranges from about 1.0:2.0:2.0 to about 1.0:2.2:2.8.

3. The process of claim 1 wherein the p-xylene-bis-(triarylphosphonium halide) is p-xylylene-bis-(triphenylphosphonium chloride).

4. The process of claim 1 wherein highly polar anhydrous organic solvent mixture is toluene and methanol.

5. The process of claim 1 wherein the organometallic base is sodium methoxide.

6. The process of claim 1 wherein the 4-carbomethoxy-benzaldehyde includes dimethyl terephthalate and methyl benzoate impurities.

7. A process for the preparation of p-xylene-bis(triphenylphosphonium chloride) wherein alpha, alpha′-dichloro-p-xylene and triphenyl phosphine are reacted in about 1:2 molar ratio without a solvent at a temperature of about 140° C. to about 200° C.

8. A process for the manufacture of 1,4-bis-[2-(4′-carbomethoxystyrenyl)]benzene which comprises reacting at a temperature of about 0° C. to about 100° C., in a highly polar anhydrous organic solvent or solvent mixture, p-xylylene-bis-(triphenylphosphonium chloride) with 4-carbomethoxybenzaldehyde, initiated by the slow introduction of the solution of an alkali metal alkoxide.

9. The process of claim 8 wherein the molar ratio of the p-xylylene-bis-(triphenylphosphonium chloride), the 4-carbomethoxybenzaldehyde and the alkali metal alkoxide ranges from about 1.0:2.0:2.0 to about 1.0:2.2:2.8.

10. The process of claim 9 wherein the solvent mixture comprises toluene and methanol.

11. The process of claim 9 wherein the alkali metal alkoxide is sodium methoxide.

* * * * *

UNITED STATES PATENT OFFICE
CERTIFICATE OF CORRECTION

Patent No. 4,537,985　　　　　　　　　Dated August 27, 1985

Inventor(s) IMRE PUSKAS  -  MARSHALL SCHMITT

It is certified that error appears in the above-identified patent and that said Letters Patent are hereby corrected as shown below:

| Column | Line | |
|---|---|---|
| 2 | 30 | "soda-mide" should be - sod-amide - |
| 3 | 17-18 | "polye-thyleneterephthalates" should be - poly-ethyleneterephthalates - |
| 5 | 48 | "EXAMPLE V" - should be centered on line 49 |
| 8 | 13-14 | "4-carbome-thoxybenzaldehyde" should be - 4-carbo-methoxybenzaldehyde - |
| 7 | 6-7 | "Identifica-　　Isomer<br>　tion No.　　of CMSB　　L　a　b" should be moved to lines 9-10 - |
| 7 | 8-10 | "Tristimulus Color....." should be - <u>Tristimulus Color</u> lines 6-8 - |
| 7 | 18 | Insert missing. - should be<br>　Identifica-　　Isomer<br>　cation No.　　of CMSB　　L　a　b　- |
| 7 | 29-31 | "Identifi-<br>　cation　　　　Isomer<br>　　No.　　　of CMSB　　L　a　b　- should be on lines 32-34 |
| 7 | 32-34 | "Tristimulus Color....." should be moved to lines 29-31 |

UNITED STATES PATENT OFFICE
CERTIFICATE OF CORRECTION

Patent No. 4,537,985     Dated August 27, 1985

Inventor(s) IMRE PUSKAS - MARSHALL SCHMITT

It is certified that error appears in the above-identified patent and that said Letters Patent are hereby corrected as shown below:

| Column | Line | | | |
|---|---|---|---|---|
| 7 | 42 | Insert missing. Indentification No. | - should be - Isomer of CMSB | L a b - |

Signed and Sealed this

Eighteenth Day of March 1986

[SEAL]

Attest:

DONALD J. QUIGG

Attesting Officer     Commissioner of Patents and Trademarks